US012637718B2

(12) United States Patent
Croucher et al.

(10) Patent No.: US 12,637,718 B2
(45) Date of Patent: May 26, 2026

(54) PREDICTIVE BIOMARKERS FOR ONVANSERTIB TREATMENT

(71) Applicant: Cardiff Oncology, Inc., San Diego, CA (US)

(72) Inventors: Peter J.P. Croucher, San Diego, CA (US); Maya Ridinger, San Diego, CA (US); Mark Erlander, San Diego, CA (US)

(73) Assignee: Cardiff Oncology, Inc., San Diego, CA (US)

( * ) Notice: Subject to any disclaimer, the term of this patent is extended or adjusted under 35 U.S.C. 154(b) by 695 days.

(21) Appl. No.: 18/078,615

(22) Filed: Dec. 9, 2022

(65) Prior Publication Data

US 2023/0183814 A1 Jun. 15, 2023

Related U.S. Application Data

(60) Provisional application No. 63/288,460, filed on Dec. 10, 2021.

(51) Int. Cl.

| | |
|---|---|
| ***C12Q 1/68*** | (2018.01) |
| ***A61K 31/517*** | (2006.01) |
| ***A61K 31/7068*** | (2006.01) |
| ***A61P 35/00*** | (2006.01) |
| ***C12Q 1/6886*** | (2018.01) |

(52) U.S. Cl.

CPC .......... *C12Q 1/6886* (2013.01); *A61K 31/517* (2013.01); *A61K 31/7068* (2013.01); *A61P 35/00* (2018.01); *C12Q 2600/156* (2013.01)

(58) Field of Classification Search

None

See application file for complete search history.

(56) References Cited

U.S. PATENT DOCUMENTS 8,927,530 B2 1/2015 Valsasina et al.

FOREIGN PATENT DOCUMENTS

WO WO2021/146322 7/2021

OTHER PUBLICATIONS

Zeidan et al; Clinical Cancer Research, vol. 26, pp. 6132-6140; Dec. 1, 2020.*

Bohl et al., "Gene expression analysis of decitabine treated AML: high impact of tumor suppressor gene expression changes", Leukemia & Lymphoma 2017, 58: 2264-2267.

Casolaro et al., "The Polo-Like Kinase 1 (PLK1) Inhibitor NMS-P937 Is Effective in a New Model of Disseminated Primary CD56+ Acute Monoblastic Leukaemia", Plos One 2013, 8:e58424.

Chen & Guestrin, "XGBoost: A Scalable Tree Boosting System", KDD '16: Proceedings of the 22nd ACM SIGKDD International Conference on Knowledge Discovery and Data Mining, Aug. 2016, pp. 785-794, https://dl.acm.org/doi/proceedings/10.1145/2939672.

Goroshchuk et al., "Polo-like kinases and acute leukemia", Oncogene 2019, 38:1-16, https://doi.org/10.1038/s41388-018-0443-5.

Liberzon et al., "Molecular signatures database (MSigDB) 3.0", Bioinformatics 2011, 12: 1739-1740.

Maiti et al., "Ten-Day Decitabine with Venetoclax (DEC10-VEN) in Acute Myeloid Leukemia: Updated Results of a Phase II Trial", Blood 2019, 134 (Supplement_1): 2637.

Stomper et al., "Can we predict responsiveness to hypomethylating agents in AML?", Seminars in Hematology 2019, 56: 118-124.

Subramanian et al., "Gene set enrichment analysis: A knowledge-based approach for interpreting genome-wideexpression profiles", PNAS 2005, 102(43): 15545-15550.

Tyner et al., "Functional Genomic Landscape of Acute Myeloid Leukemia", Nature 2018, 562(7728):526-531.

Valsasina et al., "NMS-P937, an Orally Available, Specific Small-Molecule Polo-like Kinase 1 Inhibitor with Antitumor Activity in Solid and Hematologic Malignancies" Molecular Cancer Therapeutics 2012; 11(4), 1006-16, Published Online Feb. 7, 2012; DOI: 10.1158/1535-7163.MCT-11-0765.

Welch et al., "TP53 and Decitabine in Acute Myeloid Leukemia and Myelodysplastic Syndromes", The New England Journal of Medicine 2016; 375(21): 2023-2036.

Zeidan et al., "Predictive Biomarkers of Response to the Polo-like Kinase 1 (PLK1) Inhibitor, Onvansertib, in Combination with Decitabine in Relapsed or Refractory Acute Myeloid Leukemia (R/R AML)", 63rd ASH Annua Meeting Abstracts, Blood 2021, 138: 3431-3433.

* cited by examiner

*Primary Examiner* — Jehanne S Sitton

(74) *Attorney, Agent, or Firm* — Dickinson Wright PLLC

(57) ABSTRACT

Disclosed herein include methods, compositions, and kits suitable for use in treating a hematological cancer in a subject. In some embodiments, the method comprises determining the presence or absence of at least one mutation in one or more genes encoding a spliceosome protein in sample nucleic acids from the subject; and administering onvansertib and decitabine to the subject, if the at least one mutation in one or more genes encoding a spliceosome protein is determined to be present in the sample nucleic acids, thereby reducing or inhibiting progression of the hematological cancer in the subject.

14 Claims, 2 Drawing Sheets

PREDICTIVE BIOMARKERS FOR ONVANSERTIB TREATMENT

RELATED APPLICATIONS

This application claims the benefit under 35 U.S.C. § 119(e) of U.S. Provisional Patent Application Ser. No. 63/288,460, filed Dec. 10, 2021, the content of this related application is incorporated herein by reference in its entirety for all purposes.

BACKGROUND

Field

The present disclosure relates generally to the field of cancer treatment. More specifically, therapies for treating cancer using the hypomethylating agent decitabine in combination with the PLK1 inhibitor onvansertib are provided. Methods are provided for predicting effectiveness of treatment of cancer with onvansertib and decitabine.

Description of the Related Art

Patients with relapsed or refractory acute myeloid leukemia (R/R AML) have limited therapeutic options and dismal outcomes; median overall survival is <6 months. There is a need for more effective treatments for patients suffering from hematological cancers, e.g., relapsed or refractory AML.

SUMMARY

Disclosed herein include methods for treating a subject with a cancer. In some embodiments, the method comprises: a) determining the presence or absence of at least one mutation in one or more genes encoding a spliceosome protein in sample nucleic acids from or derived from the subject; and b) administering onvansertib and decitabine to the subject, if the at least one mutation in one or more genes encoding a spliceosome protein is determined to be present in the sample nucleic acids, thereby reducing or inhibiting progression of the cancer in the subject. The cancer can be, for example, hematological cancer.

In some embodiments, the one or more genes encoding a spliceosome protein comprise SRSF2, SF3B1, ZRSR2, U2AF1, and/or U2AF2. In some embodiments, the at least one mutation comprises a mutation in the SRSF2 gene that results in a P95H mutation in SRSF2 protein, a mutation in the SF3B1 gene that results in a K700E mutation in SF3B1 protein, or both. The method can comprise determining the presence or absence of at least one mutation in TP53 gene and/or TET2 gene in the sample nucleic acids. The method can comprise not administering onvansertib and decitabine to the subject, if the at least one mutation in the TP53 gene and/or the TET2 gene is determined to be present in the sample nucleic acids. In some embodiments, each of the at least one mutation is a single nucleotide variant, an insertion mutation, a deletion mutation, an internal tandem duplication, a copy number variant, or an inversion, relative to the corresponding wild type gene.

The method can comprise obtaining the sample nucleic acids from a biological sample of the subject. In some embodiments, the biological sample comprises a bodily fluid, one or more tissues, one or more cells, or a combination thereof. In some embodiments, the bodily fluid comprises blood, plasma, urine, or a combination thereof. In some embodiments, the biological sample comprises genomic DNA, circulating tumor DNA (ctDNA), cell-free DNA (cfDNA), circulating tumor cell (CTC), RNA, or a combination thereof. In some embodiments, the biological sample comprises nucleic acids (e.g., DNA and RNA) from or derived from the subject.

In some embodiments, the biological sample comprises RNA. In some embodiments, the biological sample comprises cDNA generated from the RNA. The method can comprise determining the presence or absence of a gene expression signature in the sample nucleic acid comprising one or more markers selected from the group consisting of DF4, LBX1-AS1, ZNF3421, HTT, DHRS12, ATRN, ESPN, EBE3A, and PRRC2B; optionally. In some embodiments, the signature comprises two, three, four, five, six, seven, eight, or nine markers.

In some embodiments, step a) comprises analyzing the sample nucleic acids using polymerase chain reaction (PCR) or next generation sequencing (NGS).

In some embodiments, administering onvansertib and decitabine synergistically reduces or inhibits progression of the hematological cancer relative to onvansertib alone, decitabine alone, and/or the additive effect of onvansertib alone and decitabine alone. In some embodiments, administering onvansertib and decitabine improves one or more therapeutic effects in the subject relative to a control or a baseline. In some embodiments, the one or more therapeutic effects comprise complete remission with complete hematological recovery (CR), complete remission with incomplete hematological recovery (CRi), bone marrow response (BMR), overall response rate (ORR), or a combination thereof. In some embodiments, administering onvansertib and decitabine improves CR, CRi, BMR, ORR, or a combination thereof in the subject, relative to subjects who do not have the at least one mutation in one or more genes encoding a spliceosome protein. In some embodiments, onvansertib and decitabine are co-administered simultaneously. In some embodiments, onvansertib and decitabine are administered sequentially. In some embodiments, onvansertib is administered prior to the administration of decitabine. In some embodiments, onvansertib is administered prior to the administration of decitabine every day on which the subject is administered with onvansertib and decitabine. In some embodiments, onvansertib is administered about 30 minutes to about 5 hours prior to the administration of decitabine on a given day. In some embodiments, onvansertib and decitabine are each administered to the subject in a cycle of at least twice or at least five times within a week. In some embodiments, onvansertib is not administered on at least one day in the cycle. In some embodiments, decitabine is administered daily, weekly, bi-weekly, every three weeks, every four weeks, or every month. In some embodiments, the administration of onvansertib is oral administration and the administration of decitabine is intravenous administration.

In some embodiments, onvansertib, decitabine, or both are administered in a cycle of at least about 7 days, a cycle of at least about 21 days, or a cycle of at least about 28 days. In some embodiments, onvansertib and decitabine are administered on at least four days in the cycle. In some embodiments, the subject undergoes at least two cycles of administration of onvansertib and decitabine. In some embodiments, onvansertib is administered at 8 $mg/m^2$-90 $mg/m^2$ and decitabine is administered at 10 $mg/m^2$-25 $mg/m^2$.

In some embodiments, the decitabine is administered at a dose of about 11 $mg/m^2$, about 15 $mg/m^2$, or about 20 mg/m$^2$. In some embodiments, a maximum concentration ($C_{max}$) of onvansertib in a blood of the subject is from about 100 nmol/L to about 1500 nmol/L. In some embodiments, an area under curve (AUC) of a plot of a concentration of onvansertib in a blood of the subject over time is from about 1000 nmol/L·hour to about 400000 nmol/L·hour. In some embodiments, a time ($T_{max}$) to reach a maximum concentration of onvansertib in a blood of the subject is from about 1 hour to about 5 hours. In some embodiments, an elimination half-life ($T_{1/2}$) of onvansertib in a blood of the subject is from about 10 hours to about 60 hours.

In some embodiments, the hematological cancer is AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma, double-expressor lymphoma, anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma, chronic lymphocytic lymphoma, acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bi-phenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, myelodysplastic syndrome, or a combination thereof. In some embodiments, the hematological cancer is advanced, metastatic, refractory, or relapsed. The method can comprise one or more of (1) determining cancer status of the subject and (2) determining responsiveness of the subject to onvansertib and decitabine. In some embodiments, determining the responsiveness of the subject comprises determining if the subject is a responder of the treatment, if the subject is or is going to be in complete recovery (CR), or if the subject is or is going to be in partial remission (PR). In some embodiments, determining the responsiveness of the subject comprises determining the CR, CRi, BMR, ORR, or a combination thereof of the subject.

Disclosed herein include kits. In some embodiments, the kit comprises onvansertib and optionally decitabine. In some embodiments, the kit comprises a manual providing instructions for: a) determining the presence or absence of at least one mutation in one or more genes encoding a spliceosome protein in sample nucleic acids from a subject; and b) administering onvansertib and decitabine to the subject, if the at least one mutation in one or more genes encoding a spliceosome protein is determined to be present in the sample nucleic acids.

In some embodiments, the instructions comprise instructions for co-administrating the onvansertib and the decitabine simultaneously. In some embodiments, the instructions comprise instructions for administering the onvansertib and the decitabine sequentially. In some embodiments, the instructions comprise instructions for administering onvansertib orally and instructions for administrating decitabine intravenously. In some embodiments, the instructions comprise instructions for administering onvansertib, decitabine, or both in a cycle of at least about 7 days, a cycle of at least about 21 days, or a cycle of at least about 28 days. In some embodiments, the instructions comprise instructions for administering onvansertib, decitabine, or both on at least four days in the cycle. In some embodiments, the instructions comprise instructions for administering onvansertib at 8 mg/m$^2$-90 mg/m$^2$ and administering decitabine at 10 mg/m$^2$-25 mg/m$^2$.

DETAILED DESCRIPTION

Figure 1:
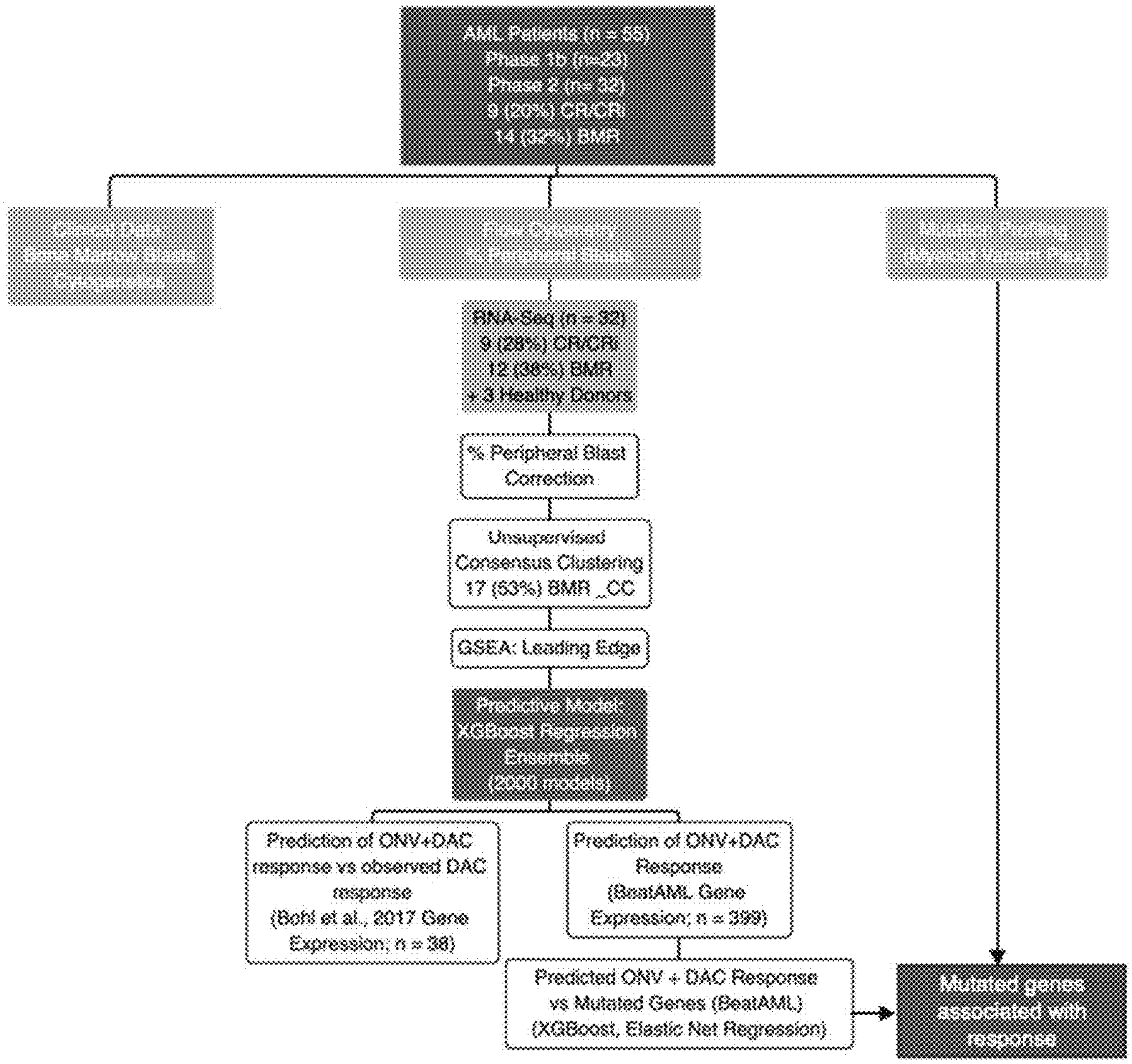
FIG. 1 depicts a non-limiting exemplary workflow of biomarker analyses used in a Phase 1b/2 clinical trial of ONV+DAC (i.e., a combination treatment using onvansertib and decitabine).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include methods, compositions, and kits for treating a subject with cancer (e.g., a hematological cancer). In some embodiments, the method comprises: a) determining the presence or absence of at least one mutation in one or more genes encoding a spliceosome protein in sample nucleic acids from the subject; and b) administering onvansertib and decitabine to the subject, if the at least one mutation in one or more genes encoding a spliceosome protein is determined to be present in the sample nucleic acids, thereby reducing or inhibiting progression of the hematological cancer in the subject.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, a "subject" refers to an animal that is the object of treatment, observation or experiment. "Animals" include cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e., Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place. In some embodiments, the patient is a human or an animal. In some embodiments, the patient is a mammal.

As used herein, "administration" or "administering" refers to a method of giving a dosage of a pharmaceutically active ingredient to a vertebrate.

As used herein, a "dosage" can refers to the combined amount of the active ingredients (e.g., PLK1 inhibitor (e.g., onvansertib) or hypomethylating agent (e.g., decitabine)) or the amount of onvansertib or the amount of decitabine.

As used herein, the term "delivery" refers to approaches, formulations, technologies, and systems for transporting a pharmaceutical composition or a therapeutic agent into the body of a patient as needed to safely achieve its desired therapeutic effect. In some embodiments, an effective amount of the composition or agent is formulated for delivery into the blood stream of a patient.

As used herein, the term "formulated" or "formulation" refers to the process in which different chemical substances, including one or more pharmaceutically active ingredients, are combined to produce a dosage form. In some embodiments, two or more pharmaceutically active ingredients can be co-formulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to a diseased tissue or a tissue adjacent to the diseased tissue. Carriers or excipients can be used to produce compositions. The carriers or excipients can be chosen to facilitate administration of a drug or pro-drug. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

As used herein, the term "pharmaceutically acceptable salt" refers to any acid or base addition salt whose counter-ions are non-toxic to the patient in pharmaceutical doses of the salts. A host of pharmaceutically acceptable salts are well known in the pharmaceutical field. If pharmaceutically acceptable salts of the compounds of this disclosure are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

As used herein, the term "hydrate" refers to a complex formed by combination of water molecules with molecules or ions of the solute. As used herein, the term "solvate" refers to a complex formed by combination of solvent molecules with molecules or ions of the solute. The solvent can be an organic compound, an inorganic compound, or a mixture of both. Solvate is meant to include hydrate, hemihydrate, channel hydrate etc. Some examples of solvents include, but are not limited to, methanol, N,N-dimethylformamide, tetrahydrofuran, dimethylsulfoxide, and water.

As used herein, "therapeutically effective amount" or "pharmaceutically effective amount" refers to an amount of therapeutic agent, which has a therapeutic effect. The dosages of a pharmaceutically active ingredient which are useful in treatment when administered alone or in combination with one or more additional therapeutic agents are therapeutically effective amounts. Thus, as used herein, a therapeutically effective amount refers to an amount of therapeutic agent which produces the desired therapeutic effect as judged by clinical trial results and/or model animal studies. The therapeutically effective amount will vary depending on the compound, the disease, disorder or condition and its severity and the age, weight, etc., of the mammal to be treated. The dosage can be conveniently administered, e.g., in divided doses up to four times a day or in sustained-release form.

As used herein, the term "treat," "treatment," or "treating," refers to administering a therapeutic agent or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition. As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire). "Pre-treatment" or "baseline," as used herein, refers to the status of a subject prior to administration of a particular therapy, e.g., onvansertib and decitabine.

Cancer

Methods, compositions and kits disclosed herein can be used for treating cancer. Methods, compositions and kits disclosed herein can be used for treating relapsed or refractory cancer. In some embodiments, a method for treating cancer comprises administrating a hypomethylating agent (e.g., decitabine) and a Polo-like kinase 1 (PLK1) inhibitor (e.g., onvansertib), or a pharmaceutically acceptable salt, solvate, stereoisomer, or prodrug thereof, to a subject (e.g., a subject with relapsed or refractory hematological cancer) in need thereof. In some embodiments, the subject has at least one mutation in one or more genes encoding a spliceosome protein.

The methods, compositions and kits disclosed herein can be used to treat various types of cancer, including but not limited to, melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer (NSCLC) and small-cell lung cancer (SCLC)), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the disease or condition provided herein includes refractory or recurrent malignancies whose growth may be inhibited using the methods and compositions disclosed herein. In some embodiments, the cancer is carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, or a combination thereof. In some embodiments, the cancer is carcinoma, squamous carcinoma (e.g., cervical canal, eyelid, tunica conjunctiva, vagina, lung, oral cavity, skin, urinary bladder, tongue, larynx, and gullet), and adenocarcinoma (e.g., prostate, small intestine, endometrium, cervical canal, large intestine, lung, pancreas, gullet, rectum, uterus, stomach, mammary gland, and ovary). In some embodiments, the cancer is sarcomata (e.g., myogenic sarcoma), leukosis, neuroma, melanoma, and lymphoma.

The cancer can be a solid tumor, a liquid tumor, or a combination thereof. In some embodiments, the cancer is a solid tumor, including but not limited to, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, Merkel cell carcinoma, brain and central nervous system cancers, and any combination thereof. In some embodiments, the cancer is a liquid tumor. In some embodiments, the cancer is a hematological cancer. The hematological cancer can be AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma, double-expressor lymphoma, anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma, chronic lymphocytic lymphoma, acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bi-phenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, myelodysplastic syndrome, or a combination thereof.

In some embodiments, the cancer is a metastatic cancer. As used herein, "metastatic cancer" can refer to when a cancer spreads (metastasizes) from its original site to another area of the body. Virtually all cancers have the potential to spread this way. Whether metastases develop depends on the complex interaction of many tumor cell factors, including the type of cancer, the degree of maturity (differentiation) of the tumor cells, the location and how long the cancer has been present, as well as other incompletely understood factors. As used herein, the term "metastasis" can refer to formation of progressively growing secondary tumor foci at sites discontinuous from the primary lesion. The metastatic process is a multi-step mechanism in which a metastatic cancer cell escapes from the primary tumor, enters the circulation, invades a distant tissue site and grows into a macroscopic tumor at the target site.

The cancer can be advanced, metastatic, refractory, or relapsed. "Refractory" as used herein can refer to a disease, e.g., cancer, that does not respond to a treatment. In some embodiments, a refractory cancer can be resistant to a treatment before or at the beginning of the treatment. In other embodiments, the refractory cancer can become resistant during a treatment. A refractory cancer is also called a resistant cancer. "Relapsed" as used herein refers to the return of a disease (e.g., cancer) or the signs and symptoms of a disease such as cancer after a period of improvement, e.g., after prior treatment of a therapy, e.g., cancer therapy.

Onvansertib and Other PLK1 Inhibitors

In some embodiments, the method comprises administering a PLK1 inhibitor (e.g., onvansertib) and a hypomethylating agent (e.g., decitabine) to the subject. Polo-like kinases (PLK) are a family of five highly conserved serine/threonine protein kinases. PLK1 is a master regulator of mitosis and is involved in several steps of the cell cycle, including mitosis entry, centrosome maturation, bipolar spindle formation, chromosome separation, and cytokinesis. PLK1 has been shown to be overexpressed in solid tumors and hematologic malignancies. PLK1 inhibition induces G2-M-phase arrest with subsequent apoptosis in cancer cells, and has emerged as a promising targeted therapy. Non-limiting examples of PLK1 inhibitor include onvansertib, BI2536, volasertib (BI 6727), GSK461364, HMN-176, HMN-214, AZD1775, CYC140, rigosertib (ON-01910), MLN0905, TKM-080301, TAK-960, Ro3280, and any combination thereof.

Onvansertib (also known as PCM-075, NMS-1286937, NMS-937, "compound of formula (I)" described in U.S. Pat. No. 8,927,530; IUPAC name 1-(2-hydroxyethyl)-8-{[5-(4-methylpiperazin-1-yl)-2-(trifluoromethoxy) phenyl]amino}-

4,5-dihydro-1H-pyrazolo[4,3-h] quinazoline-3-carboxamide) is a selective ATP-competitive PLK1 inhibitor. Biochemical assays demonstrated high specificity of onvansertib for PLK1 among a panel of 296 kinases, including other PLK members. Onvansertib has potent in vitro and in vivo antitumor activity in models of both solid and hematologic malignancies. For example, it shows high potency in proliferation assays having low nanomolar activity on a large number of cell lines, both from solid as well as hematologic tumors. Onvansertib is the first PLK1 specific ATP competitive inhibitor administered by oral route to enter clinical trials with proven antitumor activity in different preclinical models.

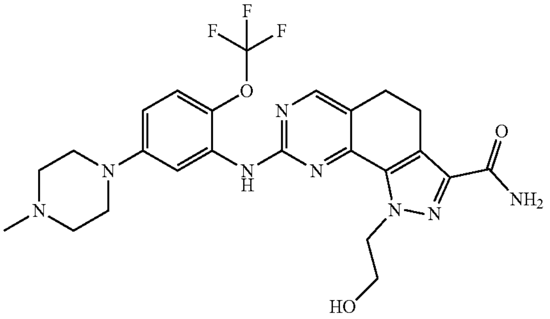

Onvansertib

Onvansertib potently causes a mitotic cell-cycle arrest followed by apoptosis in cancer cell lines and inhibits xenograft tumor growth with a clear PLK1-related mechanism of action at well tolerated doses in mice after oral administration. In addition, onvansertib shows activity in combination therapy with approved cytotoxic drugs, such as irinotecan, in which there is enhanced tumor regression in HT29 human colon adenocarcinoma xenografts compared to each agent alone, and shows prolonged survival of animals in a disseminated model of AML in combination therapy with cytarabine. Onvansertib has favorable pharmacologic parameters and good oral bioavailability in rodent and nonrodent species, as well as proven antitumor activity in different nonclinical models using a variety of dosing regimens, which may potentially provide a high degree of flexibility in dosing schedules, warranting investigation in clinical settings. Onvansertib has several advantages over previous PLK inhibitors, including high selectivity for PLK1 only, oral availability and half-life of about 24 hours.

A Phase 1 dose-escalation study with onvansertib has been conducted in adult subjects with advanced/metastatic solid tumors at a single study site in the U.S. The primary objective of that study was to determine a maximum tolerated dose (MTD) of onvansertib in adult subjects with advanced/metastatic solid tumors. Secondary objectives of the study were to define antitumor activity. In that study, a recommended phase 2 dose of 24 $mg/m^2$ was established and 5 of 16 evaluable patients had stable disease.

A phase I, first-in-human, dose-escalation study of onvansertib in patients with advanced/metastatic solid tumors identified neutropenia and thrombocytopenia as the primary dose-limiting toxicities. These hematologic toxicities were anticipated on the basis of the mechanism of action of the drug and were reversible, with recovery occurring within 3 weeks. The half-life of onvansertib was established between 20 and 30 hours. The oral bioavailability of onvansertib plus its short half-life provide the opportunity for convenient, controlled, and flexible dosing schedules with the potential to minimize toxicities and improve the therapeutic window. Pharmacodynamics and biomarker studies, including baseline genomic profiling, serial monitoring of mutant allele fractions in plasma, and the extent of PLK1 inhibition in circulating blasts, have been performed to identify biomarkers associated with clinical response and are described in WO 2021/146322, the content of which is incorporated herein by reference in its entirety.

Decitabine and Other Hypomethylating Agents

In various embodiments, the methods described herein can include administration of a hypomethylating agent to a subject. Hypomethylating agents include, but are not limited to, azacitidine (Vidaza, also known as azacytidine), decitabine (Dacogen), oral decitabine and cedazuridine (ASTX727) and guadecitabine (SGI-110). In some embodiments, the hypomethylating agent is azacitidine. In some embodiments, the hypomethylating agent is decitabine In various embodiments, the hypomethylating agent can be administered orally, intravenously or subcutaneously, as appropriate.

Azacitidine (5-azacytidine) is a chemical analogue of cytidine and is approved by the U.S. FDA for use in the treatment of myelodysplastic syndrome (MDS). Azacitidine removes methyl groups on DNA and also inhibits DNA methyltransferase, causing hypomethylation of DNA. At higher concentrations, azacitidine incorporates into DNA and RNA, resulting in direct cytotoxicity of abnormal hematopoietic cells in the bone marrow.

Decitabine (5-aza-2'deoxycitidine) is a chemical analogue of cytidine and is approved by the U.S. FDA for use in the treatment of myelodysplastic syndrome (MDS) and acute myeloid leukemia (AML). Similar to azacitidine, decitabine inhibits DNA methyltransferase, causing hypomethylation of DNA. However, decitabine is only integrated into DNA strands. Once integrated into DNA, decitabine binds irreversibly to DNA methyltransferases (DNMTs) and inhibits disengagement of the DNMTs from the DNA strand, resulting in inhibition of methylation of the DNA. The structure of decitabine is shown below:

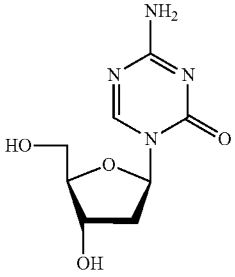

Decitabine

Detection of Spliceosome Mutations

In some embodiments, the methods described herein comprise: a) determining the presence or absence of at least one mutation in one or more genes encoding a spliceosome protein in sample nucleic acids from or derived from the subject; and b) administering onvansertib and decitabine to the subject, if the at least one mutation in one or more genes encoding a spliceosome protein is determined to be present in the sample nucleic acids, thereby reducing or inhibiting progression of the hematological cancer in the subject. The sample nucleic acids can be, or can comprise, DNA, RNA, or a combination thereof.

Extensive posttranscriptional processing is required before eukaryotic pre-mRNA matures and exits from the nucleus to the cytoplasm, including the addition of a 7-methylguanosine cap at the 5' end, the cleavage and addition of a poly-A tail at the 3' end as well as the removal of intervening sequences or introns by the spliceosome. The vast majority of higher eukaryotic genes contain multiple introns that need to be spliced out with high precision and fidelity in order to maintain the reading frame of the exons. Splicing of pre-mRNA depends on the recognition of short consensus sequences at the boundaries and within introns by an array of small nuclear ribonucleoprotein (snRNP) complexes (consisting of snRNPs U1, U2, U4, U5, U6, U11, U12m U4atc and U6atc) and a large number of proteins, including spliceosome proteins and positively as well as negatively acting splicing modulators. Mutations in spliceosome proteins are, in some embodiments, associated with cancers, including hematological cancers. As described herein, the presence of at least one mutation in one or more genes encoding a spliceosome protein in sample nucleic acids obtained from a subject can be predictive of response to treatment with a PLK1 inhibitor (e.g., onvansertib) and a hypomethylating agent (e.g., decitabine). The one or more genes encoding a spliceosome protein can comprise SRSF2, SF3B1, ZRSR2, U2AF1, and/or U2AF2.

The protein encoded by SRSF2 gene is a member of the serine/arginine (SR)-rich family of pre-mRNA splicing factors, which constitute part of the spliceosome. Each of these factors contains an RNA recognition motif (RRM) for binding RNA and an RS domain for binding other proteins. The RS domain is rich in serine and arginine residues and facilitates interaction between different SR splicing factors. In addition to being critical for mRNA splicing, the SR proteins have also been shown to be involved in mRNA export from the nucleus and in translation. SF3B1 gene encodes subunit 1 of the splicing factor 3b protein complex. Splicing factor 3b, together with splicing factor 3a and a 12S RNA unit, forms the U2 small nuclear ribonucleoproteins complex (U2 snRNP). The splicing factor 3b/3a complex binds pre-mRNA upstream of the intron's branch site in a sequence independent manner and may anchor the U2 snRNP to the pre-mRNA. Splicing factor 3b is also a component of the minor U12-type spliceosome. The carboxy-terminal two-thirds of subunit 1 have 22 non-identical, tandem HEAT repeats that form rod-like, helical structures. ZRSR2 gene encodes an essential splicing factor. The encoded protein associates with the U2 auxiliary factor heterodimer, which is required for the recognition of a functional 3' splice site in pre-mRNA splicing, and may play a role in network interactions during spliceosome assembly. U2AF1 gene belongs to the splicing factor SR family of genes. U2 auxiliary factor, comprising a large and a small subunit, is a non-snRNP protein required for the binding of U2 snRNP to the pre-mRNA branch site. This gene encodes the small subunit which plays a critical role in both constitutive and enhancer-dependent RNA splicing by directly mediating interactions between the large subunit and proteins bound to the enhancers. U2AF2 gene encodes the U2AF large subunit which contains a sequence-specific RNA-binding region with 3 RNA recognition motifs and an Arg/Ser-rich domain necessary for splicing. The large subunit binds to the polypyrimidine tract of introns early during spliceosome assembly.

Each of the at least one mutation can be a single nucleotide variant, an insertion mutation, a deletion mutation, an internal tandem duplication, a copy number variant, or an inversion, relative to the corresponding wild type gene. In some embodiments, the mutation can result in loss-of-function (lf) or gain-of-function (gf) of the protein encoded by the gene relative to the corresponding wild type protein. In some embodiments, the mutation can result in a truncated protein product. In some embodiments, the mutation is a missense mutation (e.g., results in an amino acid change at a particular residue). The at least one mutation can comprise a mutation in the SRSF2 gene that results in a P95H mutation in SRSF2 protein, a mutation in the SF3B1 gene that results in a K700E mutation in SF3B1 protein, or both. The at least one mutation can be, but is not limited to, a mutation at residues K700, K66, G740, H662, and/or R625 of SF3B1. The at least one mutation can be, but is not limited to, a mutation at residues S34, Q157, and/or S34 of U2AF1. The at least one mutation can be, but is not limited to, a mutation at residue P95 in SRSF2.

In addition to genes encoding spliceosome proteins, samples can be analyzed for mutations in further genes of interest. The method can comprise determining the presence or absence of at least one mutation in TP53 gene and/or TET2 gene in the sample nucleic acids. The method can comprise not administering onvansertib and decitabine to the subject, if the at least one mutation in the TP53 gene and/or the TET2 gene is determined to be present in the sample nucleic acids.

Sample nucleic acids can also be analyzed for the presence or absence of a gene expression signature. The term "gene expression signature," as used herein can refer to a unique pattern of gene expression in a cell, e.g., in a biological sample obtained from a subject with cancer. The biological sample can comprise RNA. The biological sample can comprise cDNA generated from the RNA. The method can comprise determining the presence or absence of a gene expression signature in the sample nucleic acid cDNA, comprising one or more markers selected from the group consisting of DF4, LBX1-AS1, ZNF3421, HTT, DHRS12, ATRN, ESPN, EBE3A, and PRRC2B. The signature can comprise two, three, four, five, six, seven, eight, or nine markers.

The method can comprise obtaining the sample nucleic acids from a biological sample of the subject. The biological sample can comprise a bodily fluid, one or more tissues, one or more cells, or a combination thereof. Mutations in one or more genes encoding a spliceosome protein can be detected in a biological sample (including but not limited to a bodily fluid (e.g., a blood sample)) from a subject of interest (e.g., a subject with a hematological cancer). For example, the mutations can be detected in genomic DNA, the circulating tumor cells (CTCs), circulating tumor DNA (ctDNA), PBMC, or a combination thereof, obtained from plasma fraction, serum fraction, or both, of a blood sample. In some embodiments, the bodily sample is whole blood, serum, plasma, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine, or any combination thereof. In some embodiments, the sample is obtained from blood and fractions thereof. A sample can be isolated or obtained from a subject and transported to a site of sample analysis. The sample may be preserved and shipped at a desirable temperature, e.g., room temperature, 4° C., −20° C., and/or −80° C. A sample can be isolated or obtained from a subject at the site of the sample analysis. The subject can be a human, a mammal, an animal, a companion animal, a service animal, or a pet. The subject may not have cancer or a detectable cancer symptom. The subject may have been treated with one or more cancer therapy, e.g., any one or more of chemotherapies, antibodies, vaccines or biologics. The subject may be in remission. The subject may be suspected to have cancer or any cancer-associated genetic mutations/disorders.

The sample can comprise nucleic acids. The terms "nucleic acid" and "nucleic acid molecule" may be used interchangeably herein. The terms refer to nucleic acids of any composition, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid can be, or can be from, a plasmid, phage, autonomously replicating sequence (ARS), centromere, artificial chromosome, chromosome, or other nucleic acid able to replicate or be replicated in vitro or in a host cell, a cell, a cell nucleus, a mitochondria, or cytoplasm of a cell. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid may be used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame, "forward" strand or "reverse" strand) and double-stranded polynucleotides. The term "gene" can refer to the segment of DNA involved in producing a "gene product" such as a miRNA or a polypeptide. Generally a gene includes regions preceding and following, e.g., the coding region (leader and trailer) involved in the transcription/translation of the gene product and the regulation of the transcription/translation, as well as intervening sequences (introns) between individual coding segments (exons). A nucleotide or base generally refers to the purine and pyrimidine molecular units of nucleic acid (e.g., adenine (A), thymine (T), guanine (G), and cytosine (C)). For RNA, the base thymine is replaced with uracil. Nucleic acid length or size may be expressed as a number of bases.

A sample can include sample nucleic acids (e.g., a plurality of sample nucleic acids). The term "plurality" is used herein to mean two or more. Thus, in some embodiments, a sample includes two or more (e.g., 3 or more, 5 or more, 10 or more, 20 or more, 50 or more, 100 or more, 500 or more, 1,000 or more, or 5,000 or more) sample nucleic acids (e.g., DNAs/RNAs). A disclosed method can be used as a very sensitive way to detect a target nucleic acid present in a sample (e.g., in a complex mixture of nucleic acids such as DNAs/RNAs). In some embodiments the sample includes 5, 10, 20, 25, 50, 100, 500, $10^3$, $5\times10^3$, $10^4$, $5\times10^4$, $10^5$, $5\times10^5$, $10^6$, or $10^7$, or more, DNAs/RNAs that differ from one another in sequence. In some embodiments, the sample includes DNAs/RNAs from a cell lysate (e.g., a eukaryotic cell lysate, a mammalian cell lysate, a human cell lysate, a prokaryotic cell lysate, a plant cell lysate, and the like). For example, in some embodiments, the sample includes DNA/RNA from a cell such as a eukaryotic cell, e.g., a mammalian cell such as a human cell.

The term "sample" as used herein shall be given its ordinary meaning and shall include any sample that includes DNA and/or RNA (e.g., in order to determine the presence or absence of at least one mutation in one or more genes encoding a spliceosome protein). The sample can be derived from any source, e.g., the sample can be a synthetic combination of purified DNAs and/or RNAs; the sample can be a cell lysate, an DNA/RNA-enriched cell lysate, or DNAs/RNAs isolated and/or purified from a cell lysate. The sample can be from a subject (e.g., a patient). The sample can be from permeabilized cells. The sample can be from cross-linked cells. The sample can be in tissue sections. The sample can be from tissues prepared by crosslinking followed by delipidation and adjustment to make a uniform refractive index. A "sample" can include a target nucleic acid (e.g., target DNA/RNA) and a plurality of non-target DNAs/RNAs. In some embodiments, the target DNA/RNA is present in the sample at one copy per 10, 20, 25, 50, 100, 500, $10^3$, $5\times10^3$, $10^4$, $5\times10^4$, $10^5$, $5\times10^5$, $10^6$, or $10^7$, non-target DNAs/RNAs.

Suitable samples include but are not limited to saliva, blood, serum, plasma, urine, aspirate, and biopsy samples. The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. A sample can comprise a biological sample such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A biological sample can comprise biological fluids derived therefrom, cells (e.g., cancerous cells, infected cells) or DNAs that is obtained from such cells (e.g., a cell lysate or other cell extract comprising DNAs). In some embodiments, the source of the sample is a (or is suspected of being) a diseased cell, fluid, tissue, or organ. In some embodiments, the source of the sample is a normal (non-diseased) cell, fluid, tissue, or organ.

In some embodiments, the sample comprises cell-free nucleic acids. Cell-free nucleic acids are nucleic acids not contained within or otherwise bound to a cell or in other words nucleic acids remaining in a sample after removing intact cells. Cell-free nucleic acids include DNA, RNA, and hybrids thereof, including genomic DNA, mitochondrial DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. A cell-free nucleic acid can be released into bodily fluid through secretion or cell death processes, e.g., cellular necrosis and apoptosis. Some cell-free nucleic acids are released into bodily fluid from cancer cells e.g., ctDNA. Others are released from healthy cells. cfDNA can be obtained from a bodily fluid without the need to perform an in vitro cell lysis step, and thus presents a non-invasive option for genomic analysis. Provided herein include methods, compositions, kits and systems for detecting and/or analyzing cell free nucleic acids (e.g., ctDNA) in bodily fluid (e.g., peripheral blood) for clinical outcome prediction/determination. The methods can comprise combined analysis of single cells and cell-free nucleic acids.

Various assays (e.g., sequencing assays) can be used to detect and analyze sample nucleic acids. The methods provided herein can comprise isolation and analysis of nucleic acids from the blood (e.g., plasma and/or serum) of a subject of interest (e.g., a subject with hematological cancer), employing the use of molecular barcoding and sequencing as a readout (e.g., next generation sequencing). The nucleic acid can be obtained from a sample by known methods, and can be analyzed by methods including but not limited to polymerase chain reaction (PCR) and next generation sequencing (NGS). In some embodiments, the nucleic acids are analyzed using targeted NGS (e.g., against a specific panel of mutations). In some embodiments, the nucleic acids are analyzed using droplet digital PCR (ddPCR).

The nucleic acids can carry one or more types of mutations, for example, germline mutations, somatic mutations, or both. Germline mutations refer to mutations existing in germline DNA of a subject. Somatic mutations refer to mutations originating in somatic cells of a subject (e.g., non-germline cells). The sample nucleic acids from a subject can carry one or more mutations in one or more genes, for example one or more genes encoding a spliceosome protein. In some embodiments, the mutation can be a hematological cancer-associated spliceosome mutation. Each of the at least one mutation can be a single nucleotide variant, an insertion mutation, a deletion mutation, an internal tandem duplication, a copy number variant, or an inversion, relative to the corresponding wild type gene.

Administration

As disclosed herein, a combination therapy of a hypomethylating agent (e.g., decitabine) and a PLK1 inhibitor (e.g., onvansertib) can surprisingly result in significantly enhanced efficacy against hematological cancer in a subject that is refractory and/or recurring. The therapeutic effect can be surprisingly synergistic (i.e., more than additive, superior to the cumulated anti-cancer efficacy caused by the hypomethylating agent and the PLK1 inhibitor separately). The PLK1 inhibitor can be onvansertib. The hypomethylating agent can be decitabine. Provided herein include methods, compositions and kits for treating hematological cancer in a subject (e.g., a human patient suffering from hematological cancer). Provided herein include methods, compositions and kits for treating cancer in a subject (for example, a human patient suffering from cancer) if at least one mutation in one or more genes encoding a spliceosome protein is determined to be present in sample nucleic acids obtained from the subject. The method comprises administrating a hypomethylating agent (e.g., decitabine) and a PLK1 inhibitor (e.g., onvansertib) to the subject in a manner sufficient to inhibit progression of the cancer. For example, the onvansertib and decitabine can be administrated to a subject with cancer simultaneously, separately, or sequentially.

In some embodiments, administering the PLK inhibitor and the hypomethylating agent synergistically reduces or inhibits progression of the cancer relative to the PLK1 inhibitor treatment alone, the hypomethylating agent treatment alone, and/or the additive effect of the PLK1 inhibitor treatment alone and the hypomethylating agent treatment alone.

In some embodiments, the inhibition or reduction of cancer progression is not merely additive, but is enhanced or synergistic (that is, the inhibition is greater than the combined inhibition of progression caused by the onvansertib and decitabine alone). The enhanced or synergistic efficacy or inhibition of any combination of a hypomethylating agent and a PLK1 inhibitor of the present disclosure can be different in different embodiments. In some embodiments, the enhanced or synergistic efficacy or inhibition of any combination of a PLK1 inhibitor and a hypomethylating agent (e.g., onvansertib and decitabine) of the present disclosure is, is about, is at least, is at least about, is at most, or is at most about, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values, higher than the combined inhibition of progression caused by onvansertib and decitabine alone.

The molar ratio of the PLK1 inhibitor (e.g., onvansertib) to the hypomethylating agent (e.g., decitabine) can be, for example, about 1:200, 1:100, 1:90, 1:80, 1:70, 1:60, 1:50, 1:40, 1:30, 1:20, 1:10, 1:1, 10:1, 20:1, 30:1, 40:1, 50:1, 100:1, 1000:1, 2000:1, or 5000:1, or a number or a range between any two of these values. In some embodiments, the enhanced or synergistic efficacy or inhibition of cancer progression caused by a combination of onvansertib and decitabine is, is about, is at least, is at least about, is at most, or is at most about 20%, 30%, 40%, 50%, 60%, 70%, 80%, 90%, 100%, 110%, 120%, 130%, 140%, 150%, 160%, 170%, 180%, 190%, 200%, 250%, 300%, or a number or a range between any two of these values, higher than the combined inhibition of progression caused by decitabine alone plus onvansertib alone. For example, a combination of onvansertib and decitabine can cause a 50%, 60%, 70%, 80%, 90%, or more, inhibition of cancer progression (cancer cell viability of 50%, 40%, 30%, 20%, 10%, or less), whereas under the same conditions the combined inhibition of the decitabine alone plus the onvansertib alone can be 10%, 20%, 25%, 30%, or less) inhibition of cancer progression (cancer cell viability of 90%, 80%, 75%, 70%, or more). Thus, the enhanced or synergistic efficacy or inhibition of cancer progression caused by the combination of onvansertib and decitabine for example, 50%, 60%, 70%, 80%, 90%, 100%, or more higher than the combined inhibition of progression caused by the decitabine alone plus the onvansertib alone.

The hypomethylating agent (e.g., decitabine) and the PLK1 inhibitor (e.g., onvansertib) can be administered to the patient in any manner deemed effective to treat the cancer. The decitabine can be administered together with, or separately from, onvansertib. When administered separately, decitabine can be administered before or after the onvansertib, or in different administration cycles. The administration of onvansertib can be oral administration. The administration of the decitabine can be intravenous administration or oral administration.

The PLK1 inhibitor and the hypomethylating agent can be co-administered (i.e., simultaneously) or sequentially. In some embodiments, it can be advantageous to administer the PLK1 inhibitor (e.g., onvansertib) to the subject before the hypomethylating agent (e.g., decitabine), e.g., on one or more days, or each day, of the days on which onvansertib and the hypomethylating agent are administered to the subject. The time interval between the administration of onvansertib and the administration of the hypomethylating agent can be, for example, 30 minutes, 1 hour, 2 hours, 3 hours, 4 hours, 5 hours, 6 hours, 7 hours, 8 hours, 9 hours, 10 hours, 11 hours, 12 hours, a range between any two of these values, or any value between 30 minutes and 12 hours. In some embodiments, the PLK1 inhibitor (e.g., onvansertib) and the hypomethylating agent (e.g., decitabine) are both administered to the subject on, or on at least about, 50%, 60%, 70%, 75%, 80%, 85%, 90%, 95%, or 100% of the days in a cycle (e.g., in each cycle during the combination treatment), and optionally the onvansertib is administered to the subject prior to the decitabine on each of the days both are administered, for example onvansertib is administered 30 minutes, 1 hour, 2 hours, 3 hours, 4 hours, 5 hours, 6 hours, 7 hours, 8 hours, 9 hours, 10 hours, 11 hours, 12 hours, a range between any two of these values, or any value between 30 minutes and 12 hours, prior to the administration of decitabine.

The decitabine and onvansertib can each be administered in any schedule, e.g., once or multiple times per day or week; once, twice, three times, four times, five times, six times or seven times (daily) per week; for one or multiple weeks; etc. In some embodiments, the decitabine and onvansertib are each administered to the patient in a cycle of at least twice within a week. In other embodiments, the decitabine and onvansertib are each administered to the patient in a cycle of at least five times within a week. In some embodiments, onvansertib is administered daily, and decitabine is administered daily, weekly, bi-weekly, every four weeks, every five weeks, or monthly. In some embodiments, the decitabine is administered twice daily. In further embodiments, the patient undergoes at least two cycles of administration. The patient can undergo one cycle or more than one cycle of administrations, for example, two cycles, three cycles, three cycles, four cycles, five cycles, or more. Two adjacent cycles of administration can be continuous, i.e., no break between the last day of the first cycle and the first day of the second cycle. In some embodiments, two adjacent cycles of administration have a break between them, i.e., an interval between the last day of the first cycle and the first day of the second cycle. The break (i.e., the interval) can be or be at least, one day, two days, three days, five days, seven days, ten days, two weeks, three weeks, four weeks, one month, two months, three months, four months, five months, six months, or a number or a range between any two of these values. In some embodiments, the patient undergoes three or four cycles of administration in which each cycle comprises at least five times within a week (e.g., 5 days per week). Each of the cycle in a multi-cycle administration can have the same dosing schedule, or different. For example, one of the cycle in the multi-cycle administration can be five continuous days of daily administration of onvansertib and decitabine and two days of break in one week for four weeks, and one or more other cycles in the same multi-cycle administration be 28 continuous days of daily administration of onvansertib and decitabine in a four-week period. The onvansertib can be administered on at least four days in the cycle. In some embodiments, onvansertib is not administered on at least one day in the cycle.

The hypomethylating agent can be administered to the patient at any appropriate dosage, e.g., a dosage of about, at least or at most 0.1 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, 300 mg/kg, 400 mg/kg, 500 mg/kg, 600 mg/kg, 700 mg/kg, 800 mg/kg, 900 mg/kg, 1000 mg/kg, 1500 mg/kg, 2000 mg/kg, or a number between any two of these values. The dosage unit based on the body weight (mg/kg) can be converted to another unit (e.g., $mg/m^2$) using a conversion chart such as the body surface area (BSA) conversion chart as will be understood by a person skilled in the art. The hypomethylating agent (e.g., decitabine) can be administered at about 10 $mg/m^2$-25 $mg/m^2$. Decitabine can be administered at a dosage of about, at least or at most 10 $mg/m^2$, 11 $mg/m^2$, 12 $mg/m^2$, 13 $mg/m^2$, 14 $mg/m^2$, 15 $mg/m^2$, 16 $mg/m^2$, 17 $mg/m^2$, 18 $mg/m^2$, 19 $mg/m^2$, 20 $mg/m^2$, 21 $mg/m^2$, 22 $mg/m^2$, 23 $mg/m^2$, 24 $mg/m^2$, 25 $mg/m^2$, or a number between any two of these values. The decitabine can be administered at about 11 $mg/m^2$, about 15 $mg/m^2$, or about 20 $mg/m^2$.

The hypomethylating agent (e.g., decitabine) can be administrated to the patient once daily, twice daily, or three times daily. The hypomethylating agent can be administered daily, weekly, bi-weekly, every three weeks, every four weeks, or every month. In some embodiments, the hypomethylating agent is administered in a cycle of 7-56 days of daily, weekly, bi-weekly, tri-weekly, every four weeks, or monthly. In some embodiments, the hypomethylating agent is administered in a cycle of 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 32 days, 35 days, 42 days, 49 days, or 56 days. In some embodiments, the hypomethylating agent is administered in 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 32 days, 35 days, 42 days, 49 days, or 56 days, in a cycle. In some embodiments, the hypomethylating agent is administered in day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 52, day 53, day 54, day 55, and/or day 56. In some embodiments, the hypomethylating agent is not administered in day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 52, day 53, day 54, day 55, and/or In some embodiments, the subject has not received any prior treatment comprising administration of the hypomethylating agent. In some embodiments, the subject has received a prior treatment comprising administration of the hypomethylating agent. Any agent that can inhibit DNA methylation, now known or later discovered, can be used in these methods, including hypomethylating agents that inhibit the activity of one or more DNA methyltransferases. In some embodiments, the hypomethylating agent is azacitidine (Vidaza, also known as azacytidine), decitabine (Dacogen), oral decitabine and cedazuridine (ASTX727) or guadecitabine (SGI-110). In some embodiments, the hypomethylating agent is decitabine.

Similarly, any PLK1 inhibitor, now known or later discovered, can be used in these methods, including PLK1 inhibitors that are selective for PLK1, and PLK1 inhibitors that also inhibit the activity of other proteins. In some embodiments, the PLK1 inhibitor is a dihydropteridinone, a pyridopyrimidine, a aminopyrimidine, a substituted thiazolidinone, a pteridine derivative, a dihydroimidazo[1,5-f] pteridine, a metasubstituted thiazolidinone, a benzyl styryl sulfone analogue, a stilbene derivative, or a combination thereof. In some of these embodiments, the PLK1 inhibitor is onvansertib, BI2536, Volasertib (BI 6727), GSK461364, AZD1775, CYC140, HMN-176, HMN-214, rigosertib (ON-01910), MLN0905, TKM-080301, TAK-960 or Ro3280.

Onvansertib can be administered to the patient at any appropriate dosage, e.g., from 8 mg/m$^2$ to 90 mg/m$^2$, including but are not limited to, a dosage of less than 12 mg/m$^2$, less than or equal to 24 mg/m$^2$, or greater than 24 mg/m$^2$. In some embodiments, the onvansertib is administered to the patient at about 8 mg/m$^2$, at about 9 mg/m$^2$, at about 12 mg/m$^2$, at about 15 mg/m$^2$, at about 18 mg/m$^2$, or at a value or a range between any two of these values. In some embodiments, the onvansertib is administered at a dose of, of at most, or of at least, about 60 mg/m$^2$. In some embodiments, the onvansertib is administered to the patient daily. In some embodiments, the onvansertib is administered in a cycle of 3-10 days of daily onvansertib administration with 2-16 days with no onvansertib administration. In some embodiments, the onvansertib is administered to the patient in a cycle of at least five times within a week. The patient can undergo two, three, or four cycles of administration. In some embodiments, the patient undergoes four cycles of administration in a cycle of at least five days of daily onvansertib administration with 1-2 days with no onvansertib administration.

In some embodiments, a PLK1 inhibitor alone or in combination with a hypomethylating agent is administrated to a patient who has taken a drug holiday after undergoing one or more cycles of administration. A drug holiday as used herein refers to a period of time when a patient stops taking a PLK1 inhibitor and/or a hypomethylating agent. A drug holiday can be a few days to several months. In some embodiments, the drug holiday can be 1 week, 2 weeks, 3 weeks, 4 weeks, 5 weeks, 6 weeks, 7 weeks, 8 weeks, 9 weeks, 10 weeks, or any value or a range between any two of these values.

As can be appreciated by one of skill in the art, the amount of co-administration of the hypomethylating agent and the PLK1 inhibitor, and the timing of co-administration, can depend on the type (species, gender, age, weight, etc.) and condition of the subject being treated and the severity of the disease or condition being treated. The hypomethylating agent and the PLK1 inhibitor can formulated into a single pharmaceutical composition, or two separate pharmaceutical compositions. The active ingredients may also be entrapped in microcapsules prepared, for example, by coacervation techniques or by interracial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. In some embodiments, the onvansertib is formulated for oral administration. In some embodiments, the decitabine is formulated for intravenous administration.

Methods, compositions, kits and systems disclosed herein can be applied to different types of subjects. For example, the subject can be a subject receiving a cancer treatment, a subject at cancer remission, a subject has received one or more cancer treatment, or a subject suspected of having cancer. The subject can have a stage I cancer, a stage II cancer, a stage III cancer, and/or a stage IV cancer. In some embodiments, the subject has advanced, metastatic, refractory, or relapsed cancer. In some embodiments, at least one mutation in one or more genes encoding a spliceosome protein is determined to be present in the sample nucleic acids obtained from the subject.

The treatment of the present disclosure can comprise administration of a PLK1 inhibitor (e.g., onvansertib) for a desired duration in a cycle. The administration of onvansertib (and/or decitabine) can be daily or with break(s) between days of administrations. The break can be, for example, 1 day, 2 days, 3 days, 4 days, 5 days, 6 days, 7 days, 8 days, 9 days, 10 days, 11 days, 12 days, 13 days, 14 days, or more. The administration can be once, twice, three times, four times, or more on a day when onvansertib (and/or decitabine) is administered to the patient. The administration can be, for example, once every two days, every three days, every four days, every five days, every six days, or every seven days. The length of the desired duration can vary, for example, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, or more days. Each cycle of treatment can have various lengths, for example, at least 14 days, 15 days, 16 days, 17 days, 18 days, 19 days, 20 days, 21 days, 22 days, 23 days, 24 days, 25 days, 26 days, 27 days, 28 days, or more. For example, a single cycle of the treatment can comprise administration of the PLK1 inhibitor (e.g., onvansertib) and/or decitabine for four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, or more in a cycle (e.g., in a cycle of at least 21 days (e.g., 21 to 28 days)). In some embodiments, the treatment can comprise administration of the PLK1 inhibitor (e.g., onvansertib) and/or decitabine for, or for at least, four days, five days, six days, seven days, eight days, nine days, ten days, eleven days, twelve days, thirteen days, fourteen days, fifteen days, sixteen days, seventeen days, eighteen days, nineteen days, twenty days, or a range between any two of these values, in a cycle (e.g., a cycle of at least 21 days (e.g., 21 to 28 days)). The administration of the PLK1 inhibitor (e.g., onvansertib) and/or decitabine in a single cycle of the treatment can be continuous or with one or more intervals (e.g., one day or two days of break). In some embodiments, the treatment comprises administration of the PLK1 inhibitor (e.g., onvansertib) for five days in a cycle of 21 to 28 days.

In some embodiments, the PLK1 inhibitor (e.g., onvansertib) is administered to the subject in need thereof on twenty days (e.g., Days 1-10 and 15-24) during a 28-day cycle. The twenty days can be, for example, a continuous daily administration for ten days (e.g., Days 1-10) and another continuous daily administration (e.g., Days 15-24) for ten days, or a continuous daily administration for four sets of five days (e.g., Days 1-5, 8-12, 15-19, and 22-26), In some embodiments, for example when the patient is identified to have low tolerance to the PLK1 inhibitor (e.g., onvansertib), the PLK1 inhibitor is administered to the subject in need thereof on ten days (e.g., Days 1-5 and 15-19) during a 28-day cycle. The ten days can be, for example, a continuous daily administration for ten days (e.g., Days 1-10) or two continuous daily admiration for five days each (e.g., Days 1-5 and Days 15-19). In some embodiments, the PLK1 inhibitor (e.g., onvansertib) is administered to the subject in need thereof on five days (e.g., Days 1-5) during a 28-day cycle. In some embodiments, the PLK1 inhibitor (e.g., onvansertib) is administered to the subject in need thereof daily throughout the whole cycle (e.g., daily for 28 days in a cycle of 28 days). Depending on the needs of inhibition/reversion of cancer progression in the subject, the subject can receive one, two, three, four, five, six, or more cycles of treatment. For combination treatment, the administration cycles, dosing schedules, and/or dosage amounts of the hypomethylating agent and the PLK1 inhibitor can be the same or different. For combination treatment, the administration cycle, dosing schedule, and/or dosage amount of the hypomethylating agent can be adjusted according to the administration cycle, dosing schedule, and/or dosage amount of the PLK1 inhibitor. For example, decitabine can be administered in four 7-day cycles (e.g., daily dose on Days 1-5 and no dose on Days 6-7, repeated for 4 weeks), which corresponds to a 28-day cycle for administration of the PLK1 inhibitor (e.g., onvansertib).

The treatment can comprise administration of the PLK1 inhibitor (e.g., onvansertib) at, or at about, 6 $mg/m^2$-90 $mg/m^2$, for example, as a daily dose. For example, the treatment can comprise daily administration of the PLK1 inhibitor (e.g., onvansertib) at, or at about, 6 $mg/m^2$, 8 $mg/m^2$, 10 $mg/m^2$, 12 $mg/m^2$, 14 $mg/m^2$, 16 $mg/m^2$, 18 $mg/m^2$, 20 $mg/m^2$, 23 $mg/m^2$, 27 $mg/m^2$, 30 $mg/m^2$, 35 $mg/m^2$, 40 $mg/m^2$, 45 $mg/m^2$, 50 $mg/m^2$, 55 $mg/m^2$, 60 $mg/m^2$, 65 $mg/m^2$, 70 $mg/m^2$, 80 $mg/m^2$, 85 $mg/m^2$, 90 $mg/m^2$, a number or a range between any two of these values, or any value between 8 $mg/m^2$-90 $mg/m^2$. In some embodiments, the daily dose of the PLK1 inhibitor (e.g., onvansertib) can be adjusted (e.g., increased or decreased with the range) during the treatment, or during a single cycle (e.g., the first cycle, the second cycle, the third cycle, and a subsequent cycle) of the treatment, for the subject. In some embodiments, the PLK inhibitor (e.g., onvansertib) is administered at 12 $mg/m^2$ on twenty days (e.g., Days 1-10 and 15-24) during a 28-day cycle. In some embodiments, the PLK inhibitor (e.g., onvansertib) is administered at 15 $mg/m^2$ on ten days (e.g., Days 1-5 and 15-19) during a 28-day cycle. In some embodiments, the PLK inhibitor (e.g., onvansertib) is administered at 8 $mg/m^2$ or 10 $mg/m^2$ everyday (e.g., Days 11-28) during a 28-day cycle. In some embodiments, the daily dose of the PLK1 inhibitor (e.g., onvansertib) can be adjusted (e.g., increased or decreased with the range) during the treatment, or during a single cycle (e.g., the first cycle, the second cycle, the third cycle, and a subsequent cycle) of the treatment, for the subject. In some embodiments, the PLK1 inhibitor is administered at or at about 12 $mg/m^2$. In some embodiments, the PLK1 inhibitor is administered at or at about 15 $mg/m^2$. In some embodiments, the PLK1 inhibitor is administered at or at about 18 $mg/m^2$. In some embodiments, the onvansertib is administered at 60 $mg/m^2$ for at least four days in a cycle. In some embodiments, the onvansertib is administered at 60 $mg/m^2$ for five days in a cycle.

A maximum concentration ($C_{max}$) of the PLK1 inhibitor (e.g., onvansertib) in a blood of the subject (during the treatment or after the treatment) when the PLK1 inhibitor is administered alone or in combination with the hypomethylating agent can be from about 100 nmol/L to about 1500 nmol/L. For example, the $C_{max}$ of the PLK1 inhibitor (e.g., onvansertib) in a blood of the subject when the PLK1 inhibitor is administered alone or in combination with the hypomethylating agent can be, or be about, 100 nmol/L, 200 nmol/L, 300 nmol/L, 400 nmol/L, 500 nmol/L, 600 nmol/L, 700 nmol/L, 800 nmol/L, 900 nmol/L, 1000 nmol/L, 1100 nmol/L, 1200 nmol/L, 1300 nmol/L, 1400 nmol/L, 1500 nmol/L, a range between any two of these values, or any value between 200 nmol/L to 1500 nmol/L.

An area under curve (AUC) of a plot of a concentration of the PLK1 inhibitor (e.g., onvansertib) in a blood of the subject over time (e.g., $AUC_{0-24}$ for the first 24 hours after administration) when the PLK1 inhibitor is administered alone or in combination with the hypomethylating agent can be from about 1000 nmol/L·hour to about 400000 nmol/L·hour. For example, the AUC of a plot of a concentration of the PLK1 inhibitor (e.g., onvansertib) in a blood of the subject over time (e.g., $AUC_{0-24}$ for the first 24 hours after administration) when the PLK1 inhibitor is administered alone or in combination with the hypomethylating agent can be, or be about, 1000 nmol/L·hour, 5000 nmol/L·hour, 10000 nmol/L·hour, 15000 nmol/L·hour, 20000 nmol/L·hour, 25000 nmol/L·hour, 30000 nmol/L·hour, 35000 nmol/L·hour, 40000 nmol/L·hour, a range between any two of these values, or any value between 1000 nmol/L·hour and 400000 nmol/L·hour.

A time ($T_{max}$) to reach a maximum concentration of the PLK1 inhibitor (e.g., onvansertib) in a blood of the subject when the PLK1 inhibitor is administered alone or in combination with the hypomethylating agent can be from about 1 hour to about 5 hours. For example, the time ($T_{max}$) to reach a maximum concentration of the PLK1 inhibitor (e.g., onvansertib) in a blood of the subject when the PLK1 inhibitor is administered alone or in combination with the hypomethylating agent can be, or be about, 1 hour, 1.5 hours, 2 hours, 2.5 hours, 3 hours, 3.5 hours, 4 hours, 4.5 hours, 5 hours, a range between any two of these values, or any value between 1 hour and 5 hours.

An elimination half-life ($T_{1/2}$) of the PLK1 inhibitor (e.g., onvansertib) in a blood of the subject when the PLK1 inhibitor is administered alone or in combination with the hypomethylating agent can be from about 10 hours to about 60 hours. For example, the elimination half-life ($T_{1/2}$) of the PLK1 inhibitor (e.g., onvansertib) in a blood of the subject when the PLK1 inhibitor is administered alone or in combination with the hypomethylating agent can be, or be about, 10 hours, 15 hours, 20 hours, 25 hours, 30 hours, 35 hours, 40 hours, 45 hours, 50 hours, 55 hours, 60 hours, a range between any two of these values, or any value between 10 hours and 60 hours.

Methods for Predicting/Determining Treatment Efficacy and Status for Cancer

Disclosed herein include methods of treating cancer. In some embodiments, the method comprises: determining the presence or absence of at least one mutation in one or more genes encoding a spliceosome protein in sample nucleic acids obtained from a subject with cancer and administering a PLK1 inhibitor (e.g., onvansertib) and a hypomethylating agent (e.g., decitabine) to the subject, thereby reducing or inhibiting progression of the cancer, if the at least one mutation in one or more genes encoding a spliceosome protein is determined to be present in the sample nucleic acids obtained from the subject. In some embodiments, the presence of at least one mutation in one or more genes encoding a spliceosome protein in the sample nucleic acids obtained from a subject with cancer is predictive of response to treatment with onvansertib and decitabine in the subject (e.g., in some embodiments, the absence of the least the at least one mutation in one or more genes encoding a spliceosome protein is not predictive of a response to the treatment described herein).

The methods described herein using the combination of the decitabine and the onvansertib are expected to be effective with various cancers, including, but not limited to hematological cancers. The hematological cancer can be AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma, double-expressor lymphoma, anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma, chronic lymphocytic lymphoma, acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bi-phenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, myelodysplastic syndrome, or a combination thereof.

The method can comprise one or more of (1) determining cancer status of the subject and (2) determining responsiveness of the subject to a PLK1 inhibitor and hypomethylating agent treatment. In some embodiments, administering onvansertib and decitabine synergistically reduces or inhibits progression of the hematological cancer relative to onvansertib alone, decitabine alone, and/or the additive effect of onvansertib alone and decitabine alone. In some embodiments, administering onvansertib and decitabine improves one or more therapeutic effects in the subject relative to a control or a baseline. The one or more therapeutic effects can comprise complete remission with complete hematological recovery (CR), complete remission with incomplete hematological recovery (CRi), bone marrow response (BMR), overall response rate (ORR), or a combination thereof. In some embodiments, determining the responsiveness of the subject comprises determining if the subject is a responder of the treatment, if the subject is or is going to be in complete recovery (CR), or if the subject is or is going to be in partial remission (PR). In some embodiments, determining the responsiveness of the subject comprises determining the CR, CRi, BMR, ORR, or a combination thereof of the subject.

The terms "complete remission" or "complete recovery" as used herein can refer to the absence of extramedullary disease (e.g., leukemic cell aggregates outside of bone marrow), <5% blasts in the bone marrow, absence of circulating blasts and blasts with Auer rods (e.g., inclusion bodies), and platelets$\geq 100\times10^9$/L and neutrophils$\geq 1.0\times10^9$/L. The term "complete remission with incomplete hematologic recovery" can refer to all CR criteria except for residual neutropenia (neutrophils$<1.0\times10^9$/L) or thrombocytopenia (platelets$<100\times10^9$/L). The term "morphologic leukemia free state" (MFLS) can refer to <5% blasts in the bone marrow with no blasts with Auer rods and no extramedullary disease. The terms "partial response" or "partial remission" can refer to the presence of all hematologic criteria of CR, decrease of bone marrow blast percentage to 5% to 25%, and/or decrease of pretreatment bone marrow blast percentage by at least 50%. The term "Bone marrow response" (BMR) can refer to at least 50% decrease in bone marrow blast from baseline. In some embodiments, the term "overall response rate" (ORR) can refer to the combined CR, CRi, MFLS, and PR. In some embodiments a combined CR/CRi value is reported.

In some embodiments, the therapeutic effect comprises improvement in CR in a subject or a cohort of subjects by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to a control or baseline. In some embodiments, the therapeutic effect comprises improvement in CRi in a subject or a cohort of subjects by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to a control or baseline. In some embodiments, the therapeutic effect comprises improvement in BMR in a subject or a cohort of subjects by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to a control or baseline. In some embodiments, the therapeutic effect comprises improvement in ORR in a subject or a cohort of subjects by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to a control or baseline.

In some embodiments, administering onvansertib and decitabine improves CR, CRi, BMR, ORR, or a combination thereof in the subject, if the at least one mutation in one or more genes encoding a spliceosome protein is determined to be present in the sample nucleic acids from the subject, relative to subjects who do not have the at least one mutation in one or more genes encoding a spliceosome protein. In some embodiments, the therapeutic effect comprises improvement in CR in a subject or a cohort of subjects, if the at least one mutation in one or more genes encoding a spliceosome protein is determined to be present in the sample nucleic acids from the subject or cohort of subjects, by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to subjects who do not have the at least one mutation in one or more genes encoding a spliceosome protein. In some embodiments, the therapeutic effect comprises improvement in CRi in a subject or a cohort of subjects, if the at least one mutation in one or more genes encoding a spliceosome protein is determined to be present in the sample nucleic acids from the subject or cohort of subjects, by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to subjects who do not have the at least one mutation in one or more genes encoding a spliceosome protein. In some embodiments, the therapeutic effect comprises improvement in BMR in a subject or a cohort of subjects, if the at least one mutation in one or more genes encoding a spliceosome protein is determined to be present in the sample nucleic acids from the subject or cohort of subjects, by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to subjects who do not have the at least one mutation in one or more genes encoding a spliceosome protein. In some embodiments, the therapeutic effect comprises improvement in ORR in a subject or a cohort of subjects, if the at least one mutation in one or more genes encoding a spliceosome protein is determined to be present in the sample nucleic acids from the subject or cohort of subjects, by at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, or a number or a range between any two of these values) relative to subjects who do not have the at least one mutation in one or more genes encoding a spliceosome protein.

In some embodiments, administering onvansertib and decitabine produces a significant CR, CRi, BMR, ORR, or a combination thereof in a cohort of subjects, if the at least one mutation in one or more genes encoding a spliceosome protein is determined to be present in the sample nucleic acids from a subject or cohort of subjects, relative to subjects who do not have the at least one mutation in one or more genes encoding a spliceosome protein. In some embodiments, the therapeutic effect comprises a combined CR/CRi in a cohort of subjects of at least about 30% (e.g., about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values). In some embodiments, the therapeutic effect comprises a BMR in a cohort of subjects of at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values). In some embodiments, the therapeutic effect comprises an ORR in a cohort of subjects of at least about 50% (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values). In some embodiments, a subject having a CR/CRi, a BMR, and/or an overall response (CR/CRi/MFLS/PR) is at least 2.5 times (e.g., 2.5, 3, 3.5, 4, 4.5, 5, 5.5, 6, 6.5, 7, 7.5, 8, 8.5, 9, 9.5, 10 times, or a number or a range between any two of these values) more likely to carry the at least one mutation in one or more genes encoding a spliceosome protein than not. In some embodiments, a subject having an overall response (CR/CRi/MFLS/PR) is at least 8 times more likely to carry the at least one mutation in one or more genes encoding a spliceosome protein than not.

Compositions and Kits

Disclosed herein include kits comprising a PLK1 inhibitor (e.g., onvansertib). In some embodiments, the kit comprises onvansertib and decitabine. In some embodiments, the kit comprises a manual providing instructions for: a) determining the presence or absence of at least one mutation in one or more genes encoding a spliceosome protein in sample nucleic acids from a subject; and b) administering onvansertib and decitabine to the subject, if the at least one mutation in one or more genes encoding a spliceosome protein is determined to be present in the sample nucleic acids.

In some embodiments, the subject has or is suspected to have cancer (e.g., a hematological cancer). The hematological cancer can be AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma, double-expressor lymphoma, anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma, chronic lymphocytic lymphoma, acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bi-phenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, myelodysplastic syndrome, or a combination thereof.

The instructions can comprise instructions including any of the methods disclosed herein. The instructions can comprise instructions for co-administrating the onvansertib and the decitabine simultaneously. The instructions can comprise instructions for administering the onvansertib and the decitabine sequentially. The instructions can comprise instructions for administering onvansertib orally and instructions for administrating decitabine intravenously. The instructions can comprise instructions for administering onvansertib, decitabine, or both in a cycle of at least about 7 days, a cycle of at least about 21 days, or a cycle of at least about 28 days. The instructions can comprise instructions for administering onvansertib, decitabine, or both on at least four days in the cycle. The instructions can comprise instructions for administering onvansertib at 8 $mg/m^2$-90 $mg/m^2$ and administering decitabine at 10 $mg/m^2$-25 $mg/m^2$. The instructions can comprise instructions for administering onvansertib prior to the administration of decitabine. The instructions can comprise instructions for administering onvansertib prior to the administration of decitabine every day on which the subject is administered onvansertib and decitabine. The instructions can comprise instructions for administering onvansertib about 30 minutes to about 5 hours prior to the administration of decitabine on a given day. The instructions can comprise instructions for administering onvansertib and decitabine to the subject in a cycle of at least twice or at least five times within a week. In some embodiments, the instructions comprise instructions the onvansertib is not administered on at least one day in the cycle. The instructions can comprise instructions for administering decitabine daily, weekly, bi-weekly, every three weeks, every four weeks, or every month.

EXAMPLES

Some aspects of the embodiments discussed above are disclosed in further detail in the following examples, which are not in any way intended to limit the scope of the present disclosure.

Example 1

Spliceosome Mutations are Associated with Clinical Response in a Phase 1b/2 Study of the PLK1 Inhibitor Onvansertib in Combination with Decitabine in Relapsed or Refractory Acute Myeloid Leukemia A multicenter phase 1b/2 study (NCT03303339) was performed to assess the safety and clinical activity of onvansertib in combination with either low-dose cytarabine or decitabine in patients with relapsed or refractory acute myeloid leukemia (R/R AML). Biomarker studies, including baseline genomic and transcriptomic profiles, were performed to identify potential biomarkers associated with clinical response to onvansertib+decitabine.

Onvansertib was administered orally, in escalating doses, on days 1 through 5 in combination with decitabine (20 $mg/m^2$ intravenously over 1 hour on days 1 through 5) in a 28-day cycle. Investigators had the flexibility to shorten the cycle to 21 days if they judged that more frequent dosing could benefit the patient. In the Phase 1b, Onvansertib was investigated at six dose levels (12-90 mg/m2) in combination with decitabine. The maximum tolerated dose was established at 60 $mg/m^2$ and was subsequently used in the Phase 2.

A total of 55 patients were treated with onvansertib in combination with decitabine (ONV+DAC): 23 in the Phase 1b and 32 in the Phase 2. Of 44 evaluable patients, 9 (20%) patients achieved complete remission, with or without complete hematopoietic recovery (CR/CRi) (Table 1). Seven patients had a CR and two patients a CRi. The overall response rate (ORR), including CR, CRi, morphologic leukemia free state (MLFS), and partial response (PR) was 27% (12/44 patients). Fourteen (32%) of the 44 evaluable patients exhibited a ≥50% reduction in bone marrow myeloblasts (bone marrow response=BMR).

Of the 55 treated patients, 32 were selected for RNA-sequencing using blood samples collected at baseline. Response rates of the RNA-seq cohort are described in Table 1. Consensus clustering was explored as a way of permitting the samples to fall into consistent natural groupings based solely on the transcriptomic patterns shared among samples using the most variable (i.e. informative) genes in the molecular data. Consensus clustering identified among the 32 patients analyzed by RNA-seq, 17 bone marrow responders (BMR_CC), including the original 12 BMR, 2 patients non evaluable for BMR, and 3 no-BMR (Table 1).

A gene expression signature ("predictive model") associated with BMR_CC was derived from the RNA-seq data (FIG. 1). The gene signature model was then applied to publicly available RNASeq data from 399 patients in the BeatAML cohort. The gene expression signature predicted 241 putative responders to ONV+DAC and 158 putative non-responders in the BeatAML cohort. Mutated genes were analyzed in these 2 groups (FIG. 1). Mutated genes positively associated with predicted response to ONV+DAC in the BeatAML cohort most notably included SRSF2 (P=0.0009), GATA3, PUF60, and SMC3 (Table 2). SRSF2 and PUF60 are both splicing/spliceosome factors.

The mutational profiling of the ONV+DAC cohort was performed at baseline for all patients (n=55) using DNA from peripheral blood mononuclear cells (PBMCs) and bone marrow mononuclear cells (BMMCs). The most frequently mutated genes were ASXL1 (22%), SRSF2 (22%), TP53 (16%), NRAS (16%), FLT3_ITD (15%), FLT3_TKD (13%), TET2 (11%) and DNMT3A (11%).

Figure 2:
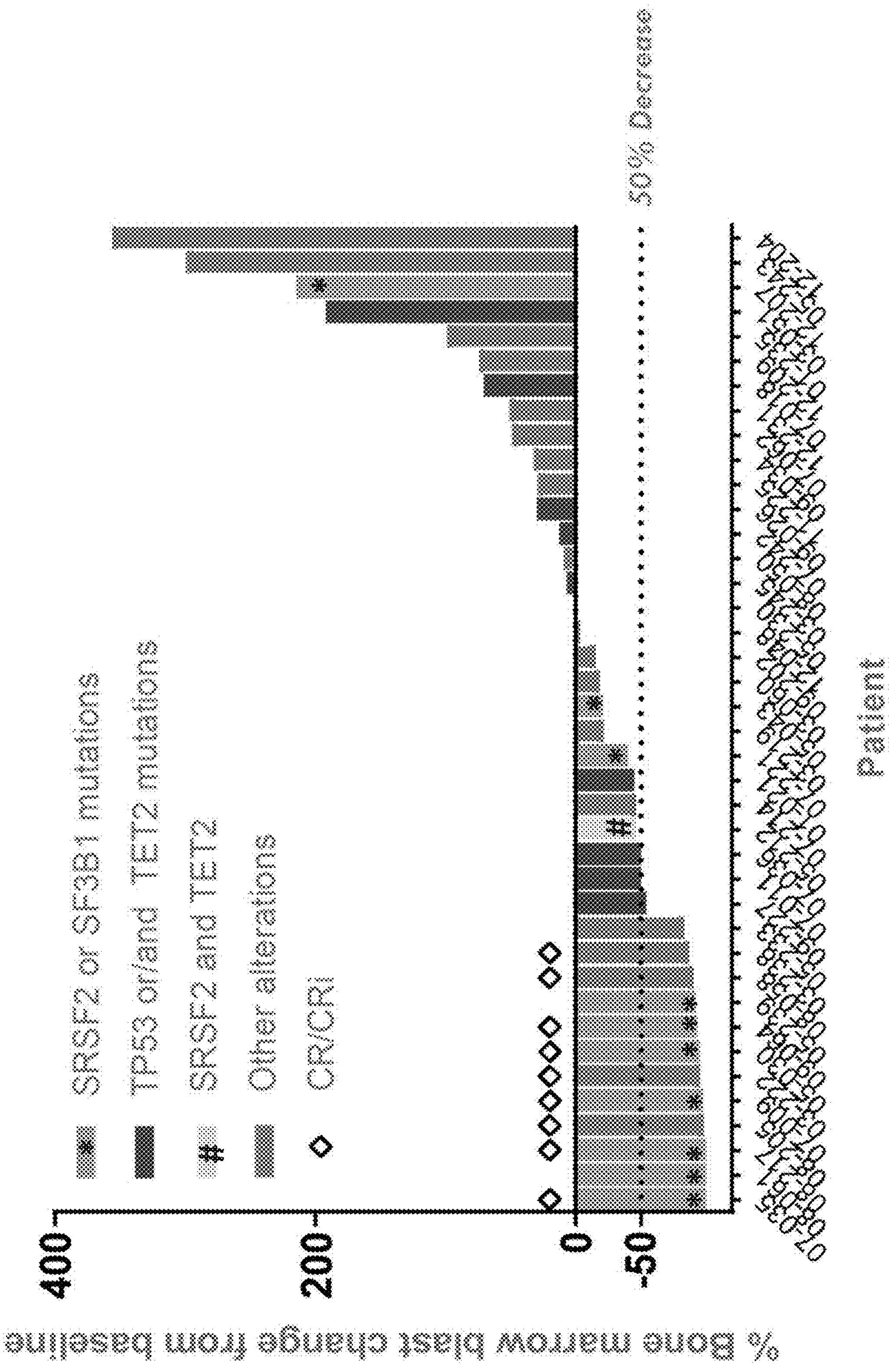
FIG. 2 depicts best bone marrow response and its association with genomic alterations in patients with evaluable bone marrow analysis. N=40.

Given the putative association observed between the predicted probability of ONV+DAC response and splice-factor genes in BeatAML, the mutational status of the core splice-factor genes SRSF2 and SF3B1 was examined in the ONV+DAC cohort. Indeed, responders (CR/CRi) were 3.49 times more likely to carry a SRSF2 or SF3B1 mutation than not, though this did not achieve statistical significance (P=0.117; Table 3). When the overall response rate was considered, responders (CR/CRi/MFLS/PR) were 8.13 times more likely to carry a SRSF2 or SF3B1 mutation than not (P=0.004; Table 3). FIG. 2 depicts best bone marrow response and its association with genomic alterations in patients with evaluable bone marrow analysis.

Altogether, these data show mutations in the spliceosome genes are associated with response to onvansertib+decitabine.

TABLE 1

CLINICAL RESPONSES TO ONV + DAC IN THE PHASE 1B/2 AML PATIENTS

| Response | All evaluable patients (n = 44) | RNA-Seq cohort (n = 32)* |
|---|---|---|
| CR/CRi | 9 (20%) | [9 (28%)] |
| ORR (CR, CRi, MLFS, PR) | 12 (27%) | [12 (38%)] |

TABLE 1-continued

CLINICAL RESPONSES TO ONV + DAC IN THE PHASE 1B/2 AML PATIENTS

| Response | All evaluable patients (n = 44) | RNA-Seq cohort (n = 32)* |
|---|---|---|
| BMR | 14 (32%) | [13 (41%)] |
| BMR CC | NA | [17 (53%)] |

CR/CRi = complete remission with or without incomplete hematopoietic recovery
ORR = overall response rate
MLFS = morphologic leukemia free-state
PR = partial response
BMR = bone marrow response
BMR_CC = Consensus Clustered BMR
*Note,
the RNASeq subset was selected to enrich BMR and therefore does not reflect actual population response rates.

TABLE 2

MULTIPLE LINEAR REGRESSION OF 27 MUTATED AML GENES ASSOCIATED WITH GENE-EXPRESSION PREDICTED ONV + DAC RESPONSE IN BEATAML

| Mutated Gene | Coefficient | P-value |
|---|---|---|
| SRSF2 | 0.0929 | 0.0009*** |
| GATA3 | 0.1383 | 0.0764 |
| PUF60 | 0.1185 | 0.0900 |
| SMC3 | 0.0952 | 0.0902 |
| MTA2 | 0.1116 | 0.2231 |
| TEX15 | 0.0758 | 0.2849 |
| RUNX1 | 0.0395 | 0.1363 |
| ASXL1 | 0.0248 | 0.4175 |
| DNMT3A | 0.0070 | 0.7319 |
| WT1 | 0.0028 | 0.9192 |
| FLT3.ITDpositive | −0.0002 | 0.9928 |
| TP53 | −0.0221 | 0.4318 |
| JAK2 | −0.0327 | 0.4467 |
| FLT3(TKD) | −0.0274 | 0.2355 |
| IDH2 | −0.0318 | 0.2217 |
| PTPN11 | −0.0551 | 0.1202 |
| TET2 | −0.0496 | 0.0399* |
| BCOR | −0.0643 | 0.0587 |
| CEBPA | −0.0694 | 0.0304* |
| LRRCC1 | −0.1272 | 0.0997 |
| CCND3 | −0.1036 | 0.0579 |
| GATA2 | −0.0914 | 0.0302* |
| NPM1 | −0.0636 | 0.0042** |
| FILIP1 | −0.1770 | 0.0426* |
| PML-RARA | −0.1265 | 0.0057** |
| GRIK2 | −0.1958 | 0.0306* |
| ZFHX4 | −0.2687 | 0.0023** |

(N = 399) Mutated genes associated (importance) with predicted response were selected by regularized regression (elastic net) and a simple XGBoost regression model and then summarized by simple multivariate linear regression as shown here.

TABLE 3

CLINICAL RESPONSES TO ONV + DAC IN RELATION TO SPLICE-FACTOR MUTATIONS

| | SRSF2 or SF3B1 mutations (n = 14) | Other mutations (n = 30) | Total (n = 44) | Odds Ratio (95% CI) | P-value |
|---|---|---|---|---|---|
| CR/CRi | 5 (36%) | 4 (13%) | 9 (20%) | 3.49 (0.61-21.97) | 0.117 |
| ORR | 8 (57%) | 4 (13%) | 12 (27%) | 8.13 (1.58-51.02) | 0.004 |
| BMR | 7 (50%) | 7 (23%) | 14 (32%) | 3.19 (0.69-15.45) | 0.095 |

ORR includes CR, CRi, MLFS and PR

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating a subject with a cancer, comprising:

a) determining the presence of at least one mutation in one or more genes encoding a spliceosome protein in sample nucleic acids from a subject with a cancer, wherein the at least one mutation comprises a mutation in the SRSF2 gene that results in a P95H mutation in SRSF2 protein, a mutation in the SF3B1 gene that results in a K700E mutation in SF3B1 protein, or both;

b) administering onvansertib and decitabine to the subject determined to have the at least one mutation, thereby reducing or inhibiting progression of the cancer in the subject; and wherein the cancer is a hematological cancer.

2. The method of claim 1, comprising obtaining the sample nucleic acids from a biological sample of the subject, and wherein the biological sample comprises a bodily fluid, one or more tissues, one or more cells, or a combination thereof.

3. The method of claim 2, wherein the biological sample comprises genomic DNA, circulating tumor DNA (ctDNA), cell-free DNA (cfDNA), circulating tumor cell (CTC), RNA, or a combination thereof.

4. The method of claim 1, wherein administering onvansertib and decitabine synergistically reduces or inhibits progression of the hematological cancer relative to onvansertib alone, decitabine alone, and/or the additive effect of onvansertib alone and decitabine alone.

5. The method of claim 4, wherein administering onvansertib and decitabine improves one or more therapeutic effects in the subject relative to a control or a baseline, wherein the one or more therapeutic effects comprise complete remission with complete hematological recovery (CR), complete remission with incomplete hematological recovery (CRi), bone marrow response (BMR), overall response rate (ORR), or a combination thereof.

6. The method of claim 5, wherein administering onvansertib and decitabine improves CR, CRi, BMR, ORR, or a combination thereof in the subject, relative to subjects who do not have the at least one mutation in one or more genes encoding a spliceosome protein.

7. The method of claim 1, wherein onvansertib and decitabine are administered sequentially.

8. The method of claim 1, wherein the administration of onvansertib is oral administration and the administration of decitabine is intravenous administration.

9. The method of claim 1, wherein onvansertib, decitabine, or both are administered in a cycle of at least about 7 days, a cycle of at least about 21 days, or a cycle of at least about 28 days.

10. The method of claim 9, wherein onvansertib and decitabine are administered on at least four days in the cycle.

11. The method claim 9, wherein the subject undergoes at least two cycles of administration of onvansertib and decitabine.

12. The method of claim 1, wherein onvansertib is administered at 8 $mg/m^2$-90 $mg/m^2$ and decitabine is administered at 10 $mg/m^2$-25 $mg/m^{2.}$

13. The method of claim 1, wherein the hematological cancer is AIDS-related lymphoma, chronic lymphocytic lymphoma (CLL), non-Hodgkin's lymphoma (NHL), T-non-Hodgkin lymphoma (T-NHL), Diffuse Large Cell Lymphoma (DLBCL), activated B-cell DLBCL, germinal center B-cell DLBCL, double-hit lymphoma, double-expressor lymphoma, anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma, chronic lymphocytic lymphoma, acute lymphoblastic leukemia, acute myeloid leukemia, T-cell leukemia, acute lymphoblastic leukemia, acute lymphocytic leukemia, acute monocytic leukemia, acute promyelocytic leukemia, biphenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, myelodysplastic syndrome, or a combination thereof.

14. The method of claim 1, wherein the hematological cancer is advanced, metastatic, refractory, or relapsed.

* * * * *